(12) United States Patent
Bloch et al.

(10) Patent No.: US 10,327,877 B2
(45) Date of Patent: Jun. 25, 2019

(54) POWERED TOOTHBRUSH HEAD HAVING A TUFT BLOCK WITH A COMBINATION OF OSCILLATING MOTIONS

(71) Applicant: Colgate-Palmolive Company, New York, NY (US)

(72) Inventors: Brian Bloch, Hillsborough, NJ (US); Lars Ralf Rainer Lieberwirth, Glashuetten (DE)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/106,581

(22) PCT Filed: Dec. 17, 2014

(86) PCT No.: PCT/US2014/070921
§ 371 (c)(1),
(2) Date: Jun. 20, 2016

(87) PCT Pub. No.: WO2015/095371
PCT Pub. Date: Jun. 25, 2015

(65) Prior Publication Data
US 2016/0338811 A1  Nov. 24, 2016

(30) Foreign Application Priority Data
Dec. 19, 2013  (CN) .......................... 2013 1 0701288

(51) Int. Cl.
*A61C 17/34* (2006.01)
*A46B 5/00* (2006.01)
(Continued)

(52) U.S. Cl.
CPC ........ *A61C 17/3472* (2013.01); *A46B 5/0095* (2013.01); *A46B 9/04* (2013.01);
(Continued)

(58) Field of Classification Search
CPC . A46B 5/0095; A61C 17/349; A61C 17/3454; A61C 17/3472
See application file for complete search history.

(56) References Cited

U.S. PATENT DOCUMENTS 5,625,916 A * 5/1997 McDougall ........ A61C 17/3436
15/22.1
7,552,497 B2 * 6/2009 Gatzemeyer ........... A46B 13/02
15/22.1
(Continued)

FOREIGN PATENT DOCUMENTS

KR  100835151  6/2008

OTHER PUBLICATIONS

Corresponding Search Report and Written Opinion for PCT/US2014/070921 dated Feb. 25, 2015.

*Primary Examiner* — Randall E Chin

(57) ABSTRACT

A powered toothbrush head that, in one embodiment, includes a head portion including a first movable tuft block configured for holding tooth cleaning elements. The first movable tuft block is operably connected to a motor-driven drift shaft for movement. An eccentric cam formed on the shaft drives the first movable tuft block via engagement with a slot formed in the body of the first movable tuft block. The first movable tuft block is movable in a combination oscillating motion comprising vertical motion and lateral pivoting or tilting motion upon rotation of the drive shaft. A related method for oscillating the first movable tuft block is disclosed.

14 Claims, 12 Drawing Sheets

(51) Int. Cl.
*A46B 9/04* (2006.01)
*B08B 1/00* (2006.01)

(52) U.S. Cl.
CPC ........ *A61C 17/349* (2013.01); *A61C 17/3418* (2013.01); *A61C 17/3445* (2013.01); *A61C 17/3454* (2013.01); *A61C 17/3463* (2013.01); *B08B 1/002* (2013.01)

(56) References Cited

U.S. PATENT DOCUMENTS

| | | | |
|---|---|---|---|
| 7,640,614 B2 * | 1/2010 | Brown | A61C 17/349 15/22.1 |
| 7,992,244 B2 * | 8/2011 | Prineppi | A61C 17/22 15/167.1 |
| 8,302,239 B2 | 11/2012 | Lantsberg et al. | |
| 2005/0005375 A1 | 1/2005 | Blaustein et al. | |
| 2012/0137452 A1 | 6/2012 | Dickie | |
| 2013/0247312 A1 | 9/2013 | Sorrentino | |

* cited by examiner

POWERED TOOTHBRUSH HEAD HAVING A TUFT BLOCK WITH A COMBINATION OF OSCILLATING MOTIONS

CROSS-REFERENCE TO RELATED PATENT APPLICATIONS

The present application is a U.S. national stage application under 35 U.S.C. § 371 of PCT Application No. PCT/US2014/070921, filed Dec. 17, 2014, which claims priority to Chinese Patent Application No. 201310701288.0, filed on Dec. 19, 2013, the entireties of which are incorporated by reference herein.

BACKGROUND

Powered toothbrushes are known having various movable tuft blocks on which tooth cleaning elements are mounted. These toothbrushes include an electric motor driven shaft configured to impart movement to the tuft blocks. Improvements and advancements of such powered toothbrushes are desirable.

BRIEF SUMMARY

According to one embodiment, the invention may be a powered toothbrush head comprising: a head portion comprising a longitudinal axis and a cavity in a front side of the head portion; a rotatable drive shaft extending through the head portion into the cavity, the drive shaft defining a first axis of rotation and including a first cam; a first movable tuft block disposed at least partially in the cavity and having an elongated slot operably engaged with the cam; the first movable tuft block including an upper portion configured for retaining tooth cleaning elements, a lower base portion, and a reduced width intermediate portion between the upper and base portions; wherein the first movable tuft block is movable in a combination oscillating motion about the longitudinal axis comprising vertical motion and tilting motion upon rotation of the drive shaft.

According to another embodiment, the invention can be a powered toothbrush comprising: a handle portion comprising a motor; a head portion comprising a longitudinal axis, the head portion including a rear wall and lateral side walls defining an open cavity; a rotatable cylindrical drive shaft operably connected to the motor and extending through the head portion into the cavity, the drive shaft defining a first axis of rotation and having an axially offset segment defining a first cam; a first movable tuft block disposed at least partially in the cavity and having a vertically elongated slot operably engaged with the first cam; the first movable tuft block including an upper portion configured for retaining tooth cleaning elements, a lower base portion, and a reduced width intermediate portion connected between the upper and base portions; wherein the first movable tuft block is movable in a combination oscillating motion about the longitudinal axis comprising a vertical motion and a tilting motion produced by rotation of the drive shaft.

In a further embodiment, the invention can be a method for oscillating a first movable tuft block of a powered toothbrush in a brushing action, the method comprising: (a) providing a powered toothbrush having a head portion comprising a vertical axis and including a rotatable drive shaft driven by a motor, the head portion including a first movable tuft block operably coupled to the drive shaft and movable in an oscillation cycle through a bottom vertical position and a top vertical position; (b) placing the first movable tuft block in the bottom vertical position with the first movable tuft block in an upright orientation wherein a top surface of the tuft block faces upwards; (c) rotating the drive shaft; (d) pivoting the first movable tuft block outwards away from the vertical axis in a first lateral direction and into a first tilted orientation wherein the top surface of the first movable tuft block faces outwards away from the vertical axis; (e) vertically raising the first movable tuft block towards the top vertical position while at least partially maintaining the first tilted orientation; (f) pivoting the first movable tuft block inwards back toward the vertical axis and into the top vertical position wherein the first movable tuft block resumes an upright orientation; (g) pivoting the first movable tuft block outwards away from the vertical axis in a second lateral direction and into a second tilted orientation wherein the top surface of the first movable tuft block faces outwards away from the vertical axis; (h) vertically lowering the first movable tuft block towards the bottom vertical position while at least partially maintaining the second tilted orientation; and (i) pivoting the first movable tuft block inwards in the first lateral direction back towards the vertical axis and into the bottom vertical position wherein the first movable tuft block resumes an upright orientation, thereby completing one oscillation cycle of the first movable tuft block.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
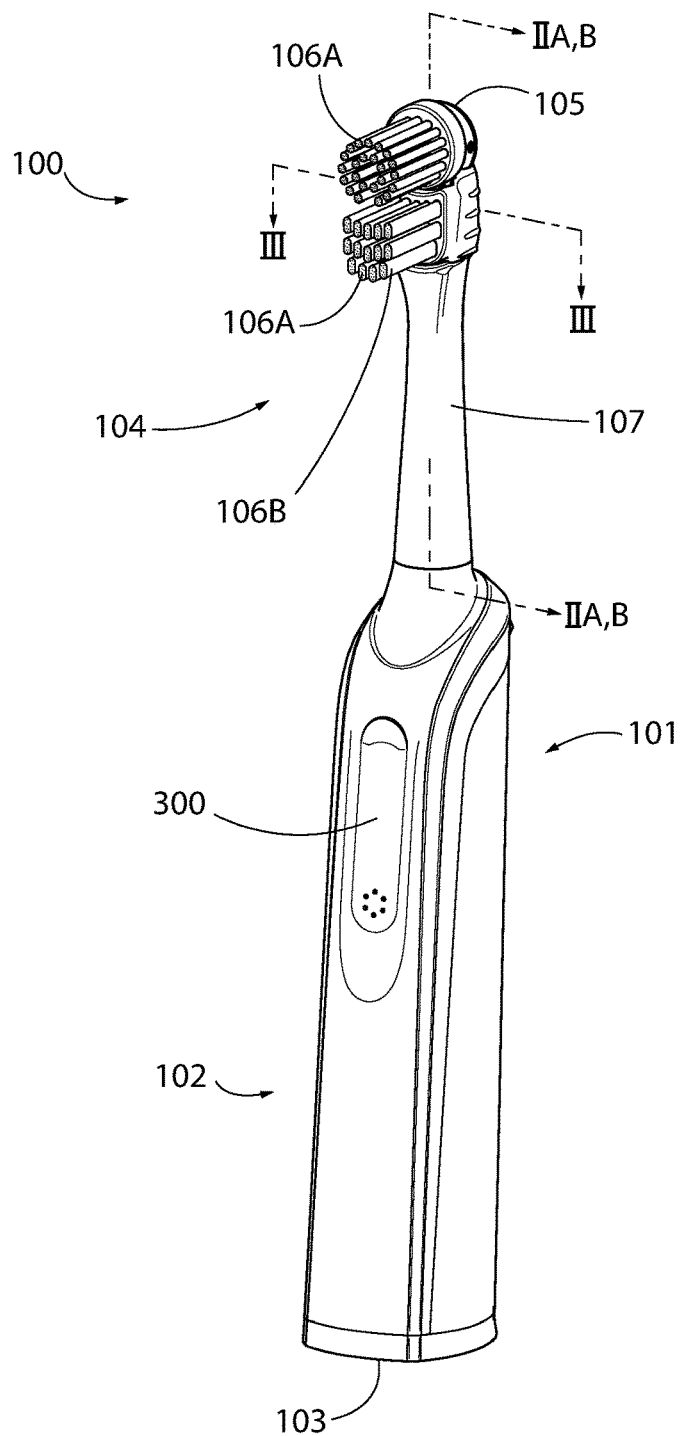
FIG. 1 is a perspective view of a powered toothbrush according to the present disclosure.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

FIG. 1 depicts a non-limiting exemplary embodiment of an oral care implement in the form of an electric-powered toothbrush 100. Toothbrush 100 includes an elongated body 101 including a handle portion 102 defining a proximal end 103, a head portion 104 defining a distal end 105, and a longitudinal axis LA extending between the proximal and distal ends. Head portion 104 supports a plurality of tooth cleaning elements 106. In one embodiment, head portion 104 may be detachably mounted to handle portion 102 to form a replaceable unit or refill thereby allowing a user to replenish the head portion after the tooth cleaning elements 106 have been worn and/or to change the type of tooth cleaning elements. Accordingly, a separable joint is formed between the head and handle portions 104, 102 of toothbrush 100 in such embodiments.

Handle portion 102 and head portion 104 of toothbrush 100 may be constructed of a material or combination of materials having suitable rigidity for grasping/handling the toothbrush and supporting the tooth cleaning elements 106, respectively. Suitable exemplary materials that may be used include, without limitation, hard plastics, such as polyethylene, polypropylene (PP), polyamide, polyester, cellulosics, SAN, acrylic, ABS and other thermoplastics suitable for toothbrush manufacture. The handle portion 102 and head portion 104 may be made of the same or different materials in various embodiments.

Figure 7:
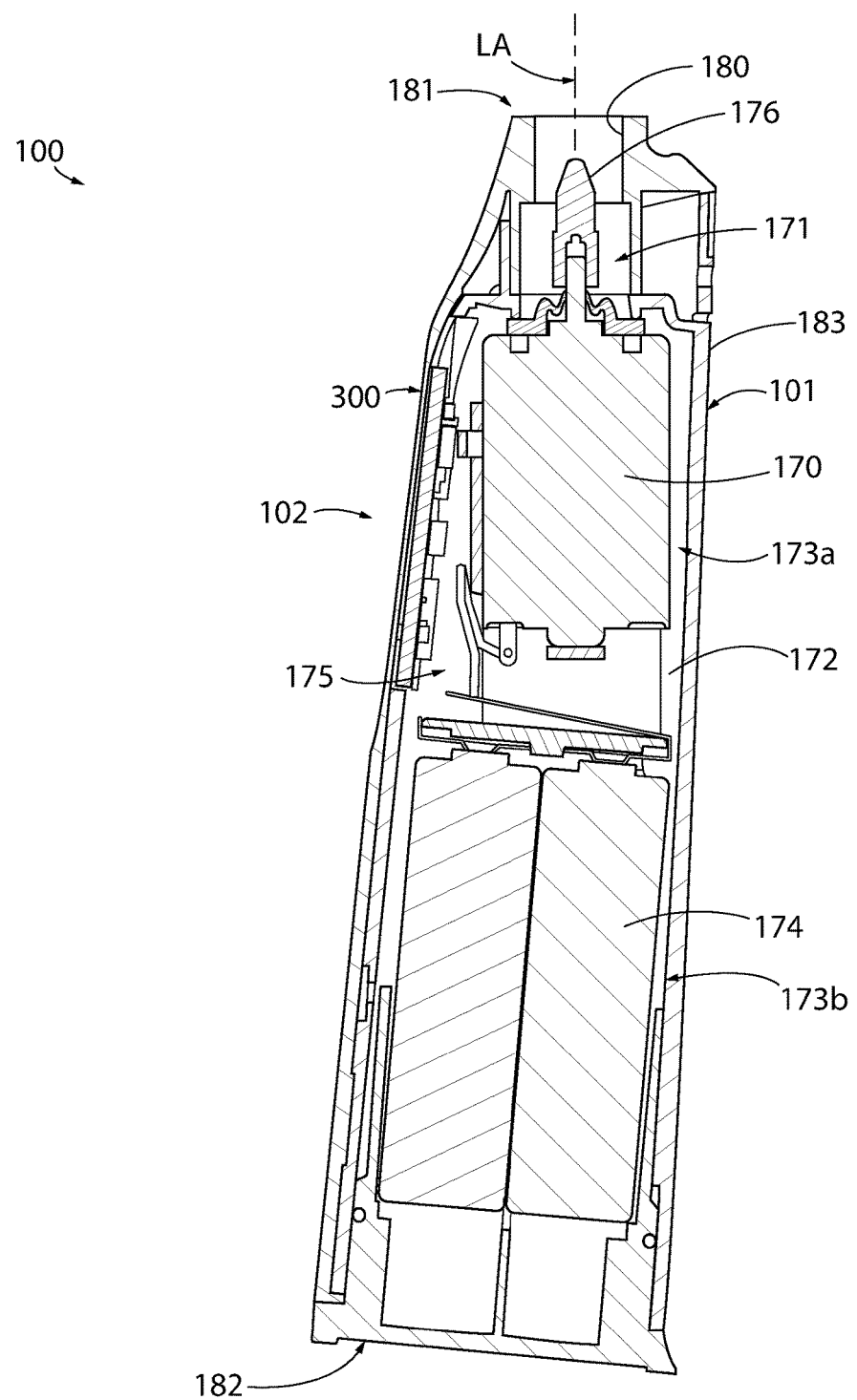
FIG. 7 is a side cross sectional view of the handle portion of toothbrush of FIG. 1.

FIG. 7 depicts a cross sectional side elevation view of toothbrush handle portion 102 alone. Referring to FIGS. 1 and 7, handle portion 102 includes a top wall 181, bottom wall 182, and side walls 183 extending between the top and bottom. Top wall 181 may include a socket 180 configured for receiving a complementary configured stem 184 on head portion 104 (see, e.g. FIGS. 2A and 2B) for mounting the head portion to the handle portion. In one embodiment, socket 180 and stem 184 may have circular cross sections; however, any suitable cross sectional shape including rectilinear and polygonal shapes may be provided (e.g. square, hexagonal, triangular, etc.).

Referring to FIGS. 1 and 7, handle portion 102 further includes an internal chamber 172 which defines a motor compartment 173a for supporting electric motor 170 and a battery compartment 173b configured for holding one or more batteries 174. Motor and battery compartments 173a, 173b may be contiguous or isolated from each other in chamber 172. Batteries 174 may be of any type including replaceable cells and/or rechargeable cells which are electrically connected to motor 170 via electrical connectors 175 which may include conductive contacts, wires, etc. Motor 170 includes a revolving rotor 171 have an end drive coupling 176 configured for detachable coupling to and driving a drive shaft 130 disposed in toothbrush head portion 104 (see, e.g. FIGS. 2A and 2B). Rotation of the motor rotor 171 in turn rotates the drive shaft 130 about its central axis CA. An operating panel 300 is provided which is electrically connected to motor 170 and includes switches or other type actuators for controlling on/off operation and/or speed of the motor.

Figure 2A:
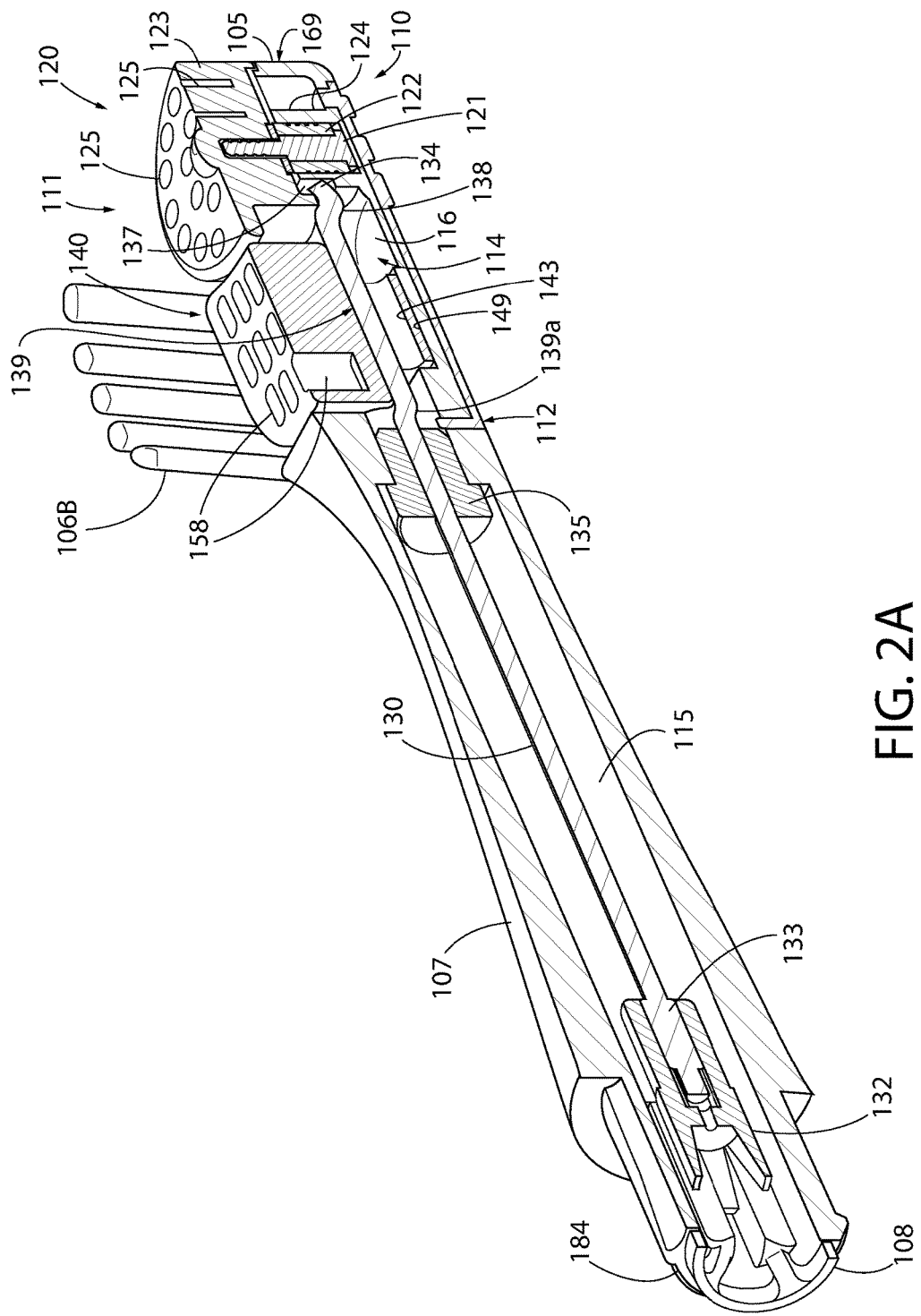
FIG. 2A is cross sectional perspective view of the head portion of the toothbrush taken along line IIA-IIA in FIG. 1.
Figure 2B:
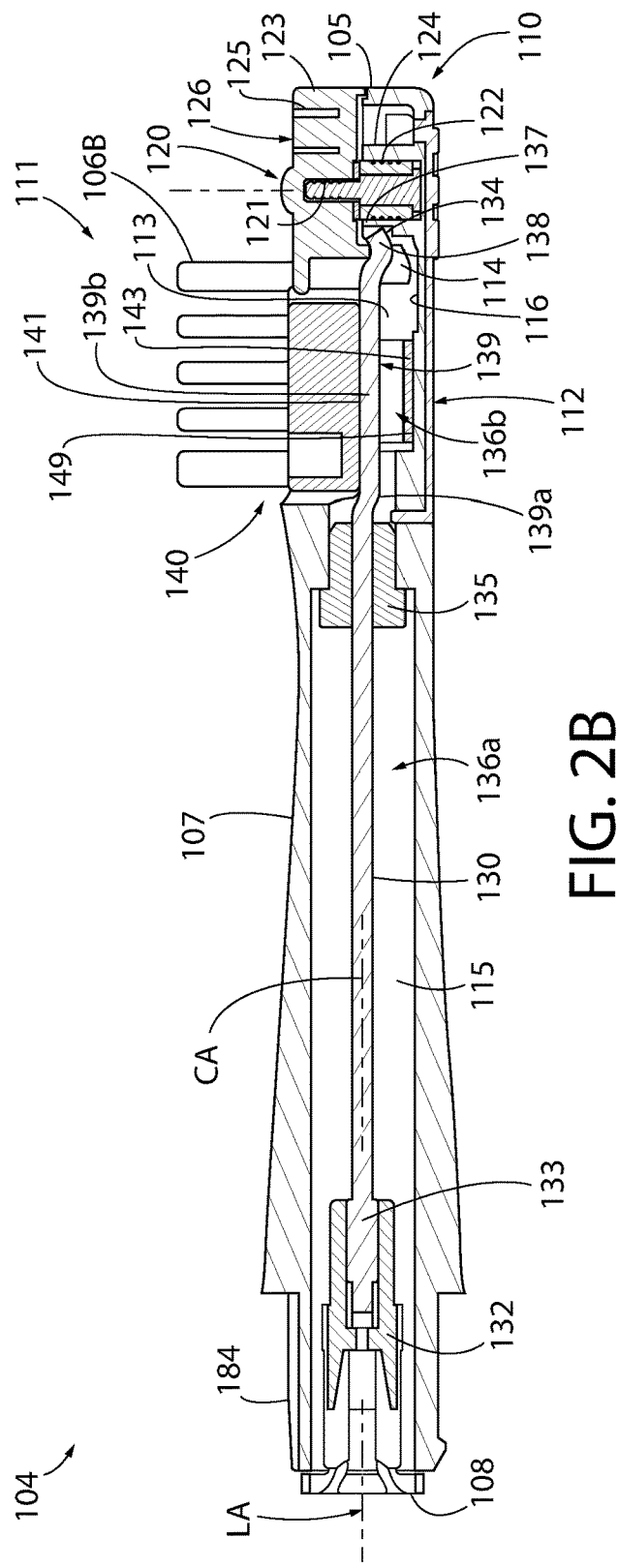
FIG. 2B is a side cross sectional view of the head portion of the toothbrush taken along line IIB-IIB in FIG. 1.
Figure 3:
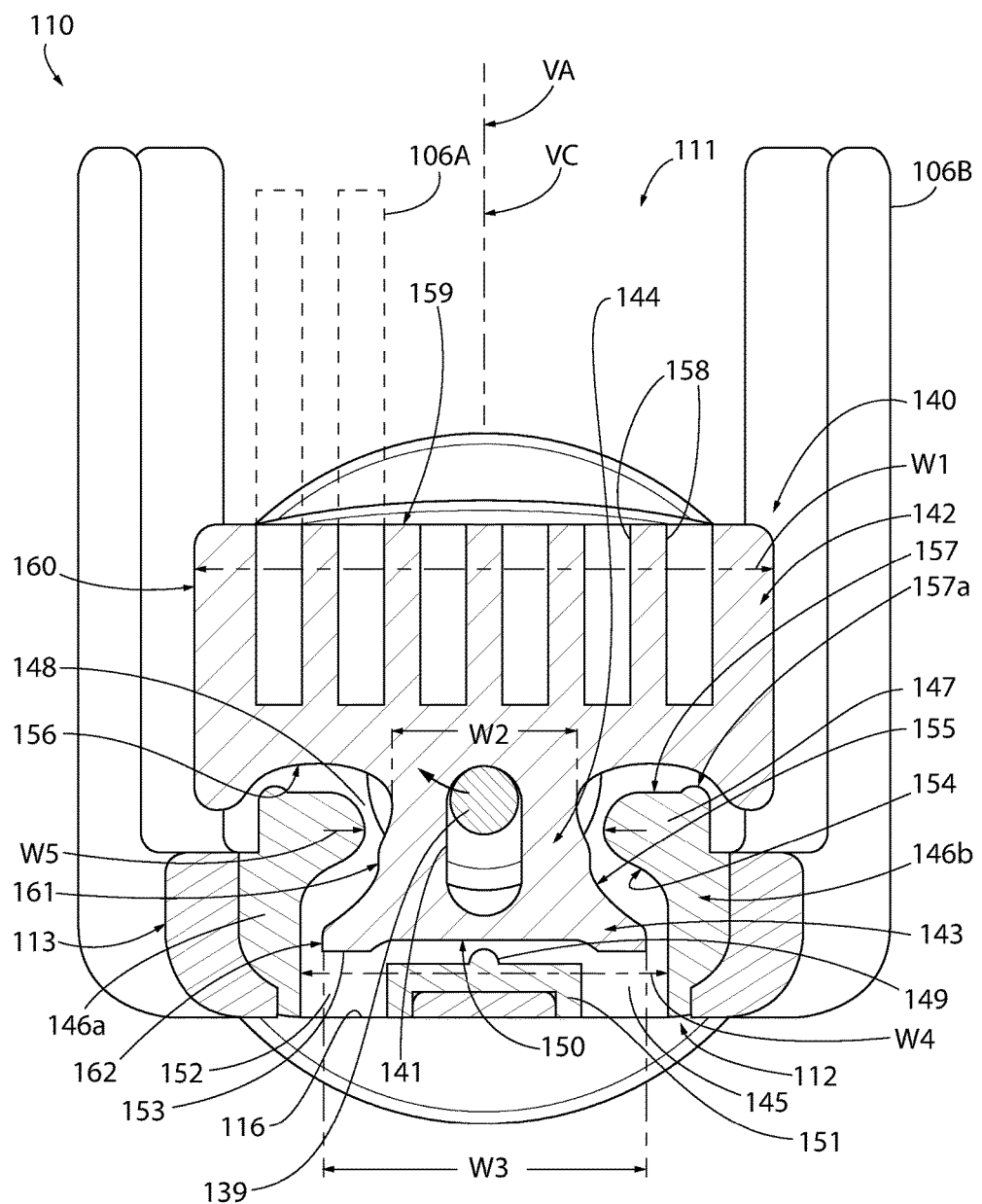
FIG. 3 is a transverse cross sectional view of a movable tuft block taken along line III-III in FIG. 1.

FIGS. 2A and 2B depict cross sectional perspective and side elevation views of toothbrush head portion 104 alone. FIG. 3 depicts a transverse cross section taken along line III-III in FIG. 1 through one of the tuft blocks 140. In one configuration, head portion 104 includes a head 110 and an elongated neck 107 connected to the head. Neck 107 defines an open proximal end 108 of head portion 104 lying along longitudinal axis LA opposite distal end 105 of toothbrush 100 which is defined by head 110. Proximal end 108 is configured for detachable mounting to a distal end 109 of the handle portion 102.

Toothbrush head 110 comprises a front side 111, an opposing rear wall 112, and opposing lateral side walls 113 extending around the periphery of the head. The rear and side walls 112, 113 define an internal cavity 114 which is open through the front side 111 of the head 110 and configured to receive tuft blocks 120, 140, as further described herein. Cavity 114 may therefore have a closed bottom surface 116 formed by rear wall 112 of head 110 and open top 117 facing and extending through the front side 111 of the head.

The rear walls 112 and lateral side walls 113 of head 110 can take on a wide variety of shapes and contours, none of which are limiting of the present invention. For example, these walls can be planar, contoured, or combinations thereof. Head 110 may be laterally widened in a direction transverse to longitudinal axis LA in contrast to neck 107 in some embodiments for supporting a variety of tooth cleaning elements 106.

In the exemplary embodiment, the neck 107 and head 110 of head portion 104 may be integrally formed as a single unitary structure using a molding, milling, machining and/or other suitable fabrication processes. However, in other embodiments the neck 107 and head 110 may be formed as separate components which are then connected at a later stage of the manufacturing process by any suitable technique known in the art, including without limitation thermal or ultrasonic welding, a tight-fit assembly, a coupling sleeve, threaded engagement, adhesion, or fasteners. Whether the head 110 and the handle 120 are of a unitary or multi-piece construction (including connection techniques) is not limiting of the present invention, unless specifically claimed.

Head 110 of toothbrush 100 is configured and structured to support a plurality and variety of different tooth cleaning elements 106 from the front side 111. As used herein, the term "tooth cleaning elements" is used in a broad generic sense to refer to any structure whatsoever that can be used to clean, polish, scrape, or wipe the teeth and/or soft oral tissue (e.g. tongue, cheek, gums, etc.) through relative surface contact. Examples of tooth cleaning elements that may be used include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient materials suitable for uses in an oral hygiene apparatus. The tooth cleaning elements 106 may be attached to head 110 by any suitable method used in the art. For example, without limitation, in-mold tufting (IFT) or anchor free tufting (AFT) could be used to mount the cleaning elements. Accordingly, invention is not limited by the types of tooth cleaning elements 106 provided or method of anchoring those elements to head 110 of head portion 104.

In one non-limiting embodiment, neck 107 may be generally tubular shaped having a circular and annular transverse cross section which may vary in diameter along the length of the neck in some configurations. Numerous other variations in the shape and configuration of neck 107 are possible. Neck 107 defines a longitudinally extending internal passageway 115 which extends through the neck from open proximal end 108 of head portion 104 into open cavity 114 formed in the head 110. Passageway 115 therefore communicates with cavity 114.

Referring to FIGS. 2A-B and 3, a drive shaft 130 is rotatably disposed inside head portion 104. Drive shaft 130 extends through internal passageway 115 from a point near proximal end 108 towards distal end 105 along longitudinal axis LA. In one embodiment, drive shaft 130 has a driven proximal section 136a disposed in neck 107 which may be substantially straight in one non-limiting embodiment and a working distal section 136b projecting into open cavity 114 of head 110 that is configured for operating movable tuft blocks 120, 140, as further described herein. Proximal end 133 of drive shaft 130 includes an adapter coupling 132 configured for detachably engaging drive coupling 176 of motor 170 disposed in handle portion 102 (see FIG. 7), thereby coupling the drive shaft to the motor. Rotation of the motor rotor 171 in turn rotates the drive shaft 130 about its central axis CA. In various embodiments, central axis CA may be concentrically aligned with or parallel to longitudinal axis LA. A bearing 135 may be disposed between the proximal and distal sections 136a, 136b of the drive shaft 130 near the conjuncture between the neck 107 and head 110 for supporting the drive shaft 130. This helps support the working distal section 136b against transverse or shear forces imposed on the drive shaft 130 when a user is brushing and presses the tooth cleaning elements 106A against their oral surfaces.

Toothbrush head 110 may include one or more powered movable tuft blocks 120 and 140 which are engaged by distal section 136b of drive shaft 130. Tuft blocks 120, 140 are each configured for mounting a plurality of moving tooth cleaning elements 106A thereto, as further described herein. Each shaft-driven tuft block 120, 140 may include tooth cleaning elements 106A in the form of bristles and/or elastomeric cleaning elements. Head 110 may further include non-motor-driven fixed or stationary tooth cleaning elements 106B in addition to any movable tuft blocks provided. The stationary tooth cleaning elements 106B may similarly include bristles and/or elastomeric cleaning elements. As used herein, the terms "movable" tuft blocks and "moving" tooth cleaning elements refers to tuft blocks and tooth cleaning elements which have motion produced via operation of a power drive (e.g. motor) without contact with a user's oral surfaces (e.g. teeth, gums, etc.) during brushing to impart movement. The terms "fixed" or "stationary" tooth cleaning elements refers to elements that are static when not in contact with a user's oral surfaces and move primarily only as a result of the tooth brushing action.

Referring to FIGS. 2 and 3, tuft block 120 may be a distal-most tuft block disposed near distal end 105 and end wall 169 of toothbrush head 110. In one embodiment, tuft block 120 may be an oscillating type tuft block as described U.S. Pat. No. 5,625,916, which is incorporated herein by reference in its entirety. Tuft block 120 is rotationally and arcuately movable back and forth in reversible directions through a limited arcuate path around a center support spindle 121 which is oriented transversely to longitudinal axis LA and defines an axis of rotation. Spindle 121 may be mounted in and supported by a suitable bearing 122 disposed in receptacle 124 formed inside cavity 114 to provide smooth rotational movement of the spindle. In some embodiments, a majority of tuft block 120 may be generally positioned in open cavity 114 formed in head 110.

In one embodiment, tuft block 120 is actuated and operated by a first angular offset segment formed by a curved or eccentric distal end 134 of drive shaft 130 which defines a first eccentric cam 138. Cam 138 may have a generally hooked configuration which includes a double bend having a first portion bent outwards away from the central axis CA of drive shaft 130 and a second portion bent back inwards towards the central axis CA. Cam 138 engages an operating slot 137 formed in a side of tuft block 120. Rotation of drive shaft 130 through 360 degrees oscillates or pivots tuft block 120 back and forth transversely to longitudinal axis LA of toothbrush 100 through an arcuate path of motion around spindle 121. In one representative but non-limiting example, the arcuate path of motion may be between about and including 10-90 degrees, and more particularly 20-30 degrees in some embodiments.

As shown in FIGS. 2A and 2B, tuft block 120 includes a plurality of openings 125 formed in an outward facing top surface 126 of an upper bristle holding portion 123 which are configured for inserting and mounting bristle tufts and/or elastomeric cleaning elements through the openings. Openings 125 may be of any suitable shape (in top plan view). Tuft block 120 may have any suitable configuration. In one non-limiting embodiment, tuft block 120 may have a circular shape in top plan view. Numerous other variations in shape are possible.

Referring initially to FIGS. 2A-B and 3, tuft block 140 in one non-limiting exemplary embodiment may be generally T-shaped or mushroom-shaped in transverse cross section. Toothbrush 140 includes an upper bristle holding portion 142, a lower base portion 143, and a narrowed reduced width intermediate portion 144 between portions 142 and 143. Bristle holding portion 142 has a vertical height sufficient for mounting bristles and/or elastomeric tooth cleaning members. A plurality of openings 158 formed in an outward facing top surface 159 of an upper bristle holding portion 142 are configured for inserting and mounting bristle tufts and/or elastomeric cleaning elements such as tooth cleaning elements 106A (illustrated in dashed lines) through the openings. Openings 158 may be any suitable shape (in top plan view). Top surface 159 extends transversely to longitudinal axis LA between the opposing lateral sides 160. In one embodiment, top surface 159 may be substantially flat; however, arcuately curved or undulating profiles may also be used. Tuft block 140 may be longitudinally elongated having a larger axial length (measured parallel to longitudinal axis LA) than lateral width measured between the lateral sides 160.

In one embodiment, bristle holding portion 142 has a width W1 which may be wider than width W2 of the intermediate portion 144 (measured at its narrowest point between lateral sides 161), and in some embodiments width W1 may be wider than width W3 of base portion 143 between lateral sides 162. Width W2 of intermediate portion 144 may be smaller than both widths W1 and W3 of bristle holding and base portions 142 and 143, respectively. This captures or traps the base portion 143 in a receptacle 145 formed within a portion of cavity 114 in toothbrush head 110 to prevent the tuft block 140 from being transversely extracted from the cavity through the front side 111 of the head, as further described herein.

Receptacle 145 may be formed and defined by opposing lateral walls 146a, 146b positioned in cavity 114 (see, e.g. FIG. 3). Walls 146a, 146b may be separate structures mounted inside the cavity 114 or may be formed by integral interior portions of lateral side walls 113 of the toothbrush head 110. In one embodiment, walls 146a, 146b may further define a pair of inward projecting operating flanges 147 which each extend towards longitudinal axis LA. Flanges 147 are spaced laterally/transversely apart to form a reduced width entrance 148 to receptacle 145 from front side 111 of toothbrush head 110. Entrance 148 has a lateral width W2 which is less than width W4 of receptacle 145. The free ends of flanges 147 may each have convexly curved or rounded surfaces to smoothly and slidingly engage tuft block 140, as further described herein. Portions of walls 146a, 146b below flanges 147 may be substantially vertical in one embodiment. The transition or shoulders 154 formed between flanges 147 and walls 146a, 146b may be concavely rounded to avoid sharp corners and provide a gradually contoured sliding surface configured to abuttingly and slidingly contact outwardly flared leg extensions 153 on base portion 143 of tuft block 140 for smooth movement.

A bottom portion of the receptacle 145 may further include an upwardly extending protuberance 149 formed above and generally proximate to and adjacent rear wall 112 of toothbrush head 110. Referring to FIGS. 2A-B and 3, protuberance 149 defines a pivot configured to engage a bottom surface 150 formed on base portion 143 of tuft block 140. In one embodiment, protuberance 149 may be generally shaped as a longitudinally extending ridge formed inside receptacle 145. In that configuration, protuberance 149 may have an axial length measured along the longitudinal axis LA which is substantially coextensive with the axial length of base portion 143 of tuft block 140 to restrict movement of the tuft block to a side-to-side lateral rocking motion and minimize rocking in a back and forth direction (i.e. proximal to distal) along the longitudinal axis LA. A ridge-shaped protuberance 149 may have a continuous or interrupted length and structure. Other variations in the shape and configuration of protuberance 149 however are possible. For example, in another possible embodiment, protuberance 149 may have a semi-spherical or half round shape (e.g. dimple or nub) with a limited axial length substantially less than the axial length of tuft block base portion 143.

In one embodiment, protuberance 149 may be formed on a raised pedestal 151 extending upwards from the bottom surface 116 of the cavity 114 within the confines of receptacle 145. Pedestal 151 may be a separate structure mounted inside the receptacle 145 or may be formed by integral interior portion of rear wall 112 of the toothbrush head 110. The pedestal 151 forms two pockets 152 on either lateral side for receiving laterally and outwardly flared leg extensions 153 on base portion 143 of tuft block 140 during movement of the tuft block. Leg extensions 153 extend laterally farther than intermediate portion 144 of tuft block 140.

Referring to FIG. 3, intermediate portion 144 may have generally concave curved lateral surfaces 155 for abuttingly and slidingly engaging the rounded flanges 147 formed in toothbrush head 110. This ensures smooth and unbinding motion as the tuft block 140 moves through its various positions, as further described herein. Similarly, the underside of upper bristle holding portion 142 of tuft block 140 may include concavely rounded bottom surfaces 156 contoured for smoothly engaging the top surface 157 of rounded flanges 147 formed in toothbrush head 110. The top surface may be configured to include raised longitudinally extending rails 157a to facilitate smooth non-binding contact with the underside surfaces 156 of the tuft block upper bristle holding portion 142.

In one embodiment, tuft block 140 is mounted on and actuated by a second angular offset segment formed by a curved or eccentric portion of drive shaft 130 which defines a second eccentric cam 139. Referring to FIGS. 2A, 2B, and 3, cam 139 is disposed between distal end 134 and proximal end 133 of drive shaft 130. In various embodiments, cam 139 may include at least one bend 139a as shown with an adjoining straight segment 139b having an axis which is transversely offset from and parallel to central axis CA of drive shaft 130. Cam 139 is configured and arranged to engage a vertically oriented and elongated operating slot 141 in tuft block 140 for moving the tuft block in a plurality of directions transverse to longitudinal axis LA of toothbrush 100 as the drive shaft 130 rotates. In one alternative embodiment, two bends 139a may be provided with offset straight segment 139b disposed therebetween.

It should be noted that in the embodiment shown in FIG. 3, none of the peripheral edges or sides of tuft block 140 are attached or coupled to toothbrush head 110 so that the tuft block is freely movable to translate in position vertically, laterally, and angularly (i.e. tilting) transverse to longitudinal axis LA when driven by drive shaft cam 139. This allows tuft block 140 to simulate a Bass brushing technique preferred by many oral care professionals. The sole point of coupling in the present embodiment between tuft block 140 and the toothbrush head portion 104 is via cam 139 engaging slot 141 formed in intermediate portion 144 of the tuft block. The range of vertical, lateral, and angular motion may be restricted by design via engagement between base and intermediate portions 143, 144 of tuft block 140 and flanges 147 formed in receptacle 145 of toothbrush head 110, as further described herein.

The powered operation and brushing motion created by tuft block 140 will now be described in greater detail. FIGS. 4A-I illustrate sequential "still" images showing various positions of tuft block 140 occurring during completion of a full oscillation cycle of tuft block 140 when driven by motorized drive shaft 130. It will be appreciated that these positions shown occur rapidly in a fraction of a second as part of a continuous cyclical motion produced by the rotating drive shaft and eccentric cam 139 formed thereon. In this embodiment, the oscillation cycle of brushing motion replicates the Bass brushing technique.

For clarity, all elements of tuft block 140 have not been labeled in FIGS. 4A-I for clarity to better show the positions of the tuft block in motion and interaction with various parts of the toothbrush head portion. Accordingly, reference should also be made to FIG. 3 recognizing that similarly drawn parts without labels are the same in FIGS. 4A-I as in FIG. 3.

In one exemplary embodiment, a method for moving a tuft block 140 of a powered toothbrush 100 through an oscillation cycle includes first providing a powered toothbrush 100 having a movable head portion 104. In FIGS. 4A-I, the drive shaft 130 rotates in a clockwise direction and eccentric cam 139 rotates clockwise about the drive shaft to drive tuft block 140 through the oscillation cycle. The vertical axis VA shown in FIGS. 3 and 4A-I will provide a plane of reference useful in describing the orientation of tuft block 140 during various parts of the oscillation cycle. The drive shaft 130 defines a longitudinally oriented or horizontal axis of rotation extending along longitudinal axis LA thereby providing another point of reference for describing the motion of tuft block 140. Because the top (upper bristle holding portion 142), bottom (base portion 143), and lateral sides of tuft block 140 (i.e. lateral sides 160, 161, and 162) are not physically attached to the lateral side walls 113 or bottom wall 112 of toothbrush head 110 in which the tuft block is mounted, this free floating arrangement of tuft block 140 advantageously provides three degrees of motion not being constrained to simply vertical movement or pivoting movement about a fixed pivot axis alone. Accordingly, tuft block 140 is free to move angularly (i.e. rock or tilt), vertically, and laterally (horizontally) allowing an oscillation cycle of motion to be provided by a powered toothbrush that beneficially replicates compound brushing motions (e.g. Bass motion) normally achieved by manual brushing techniques.

Figure 4A:
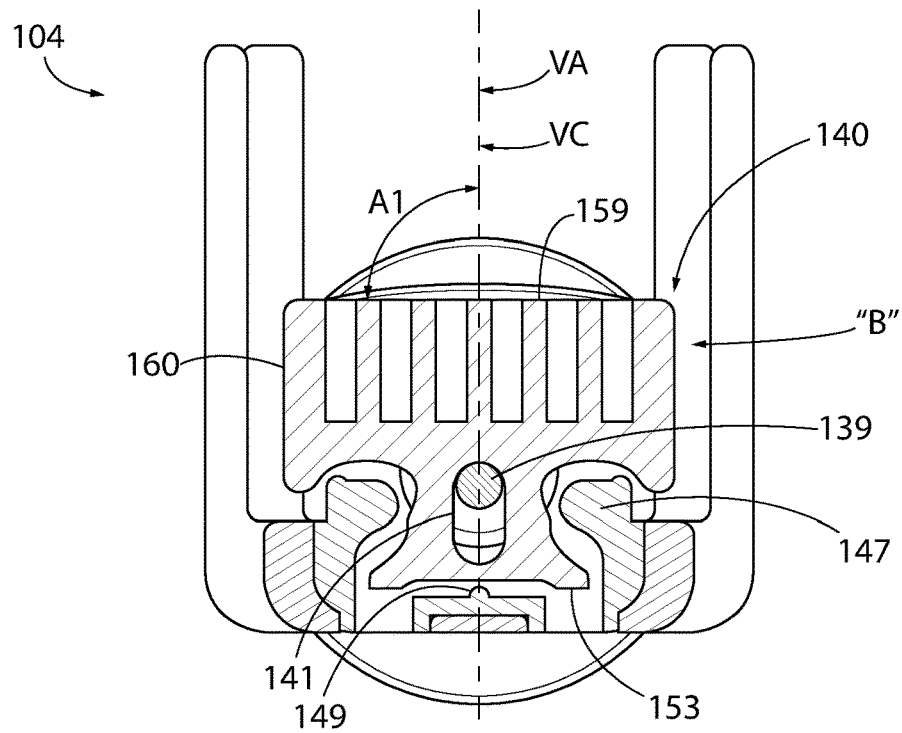
FIGS. 4A-I show sequential transverse cross sectional views of the movable tuft block of FIG. 3 during an oscillation cycle of a motor-driven brushing action.
Figure 4B:
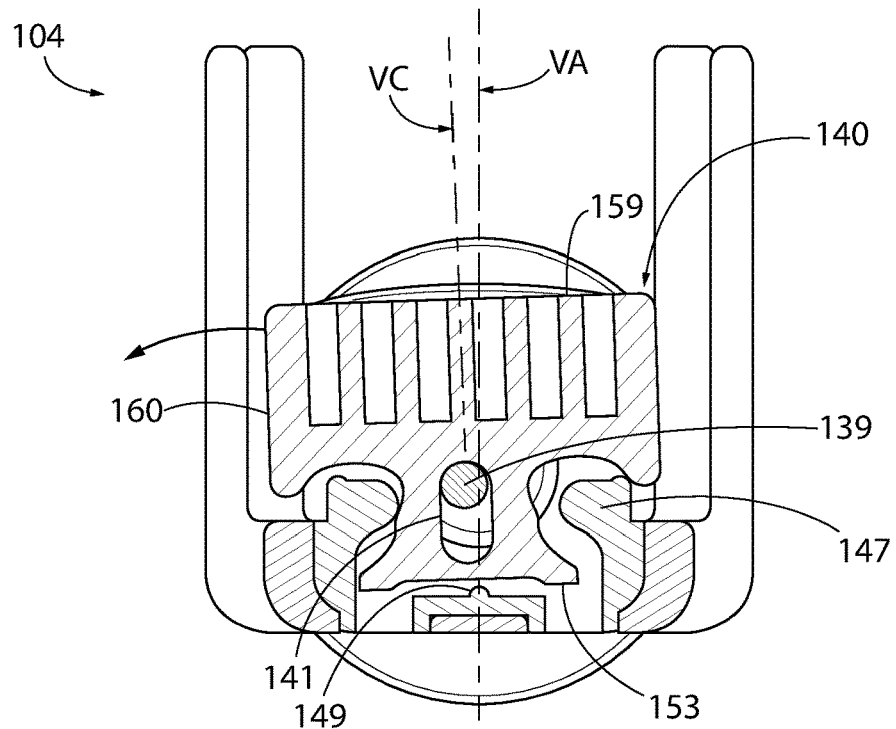
Figure 4C:
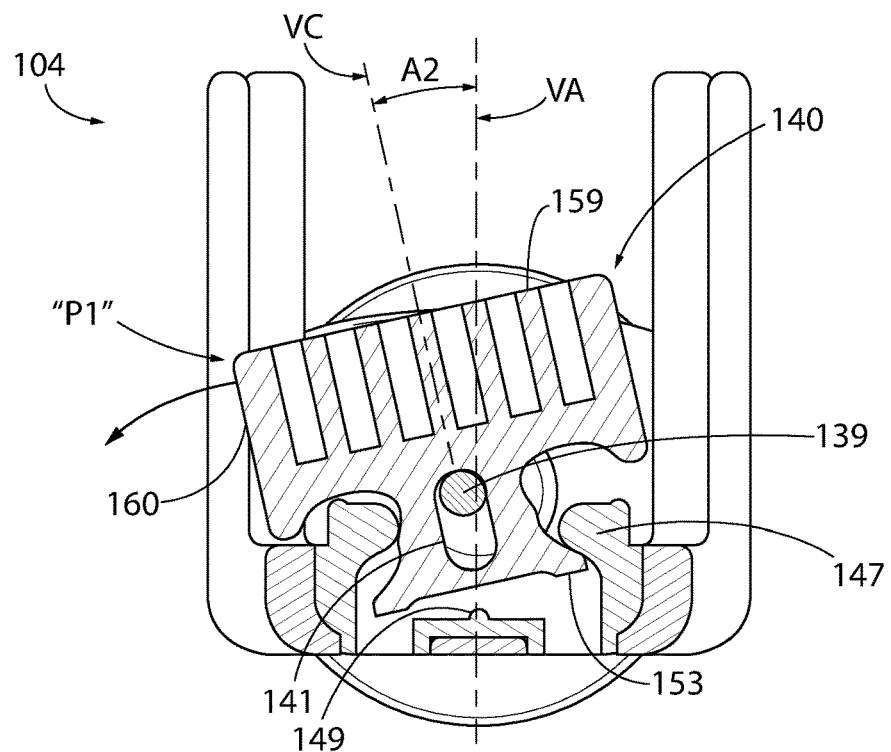
Figure 4D:
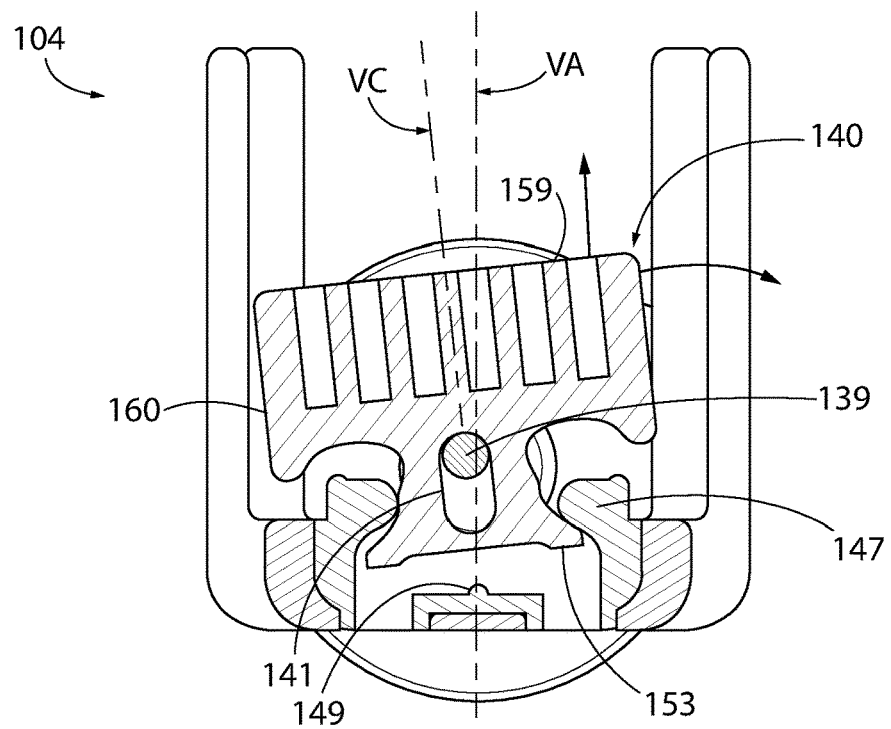
Figure 4E:
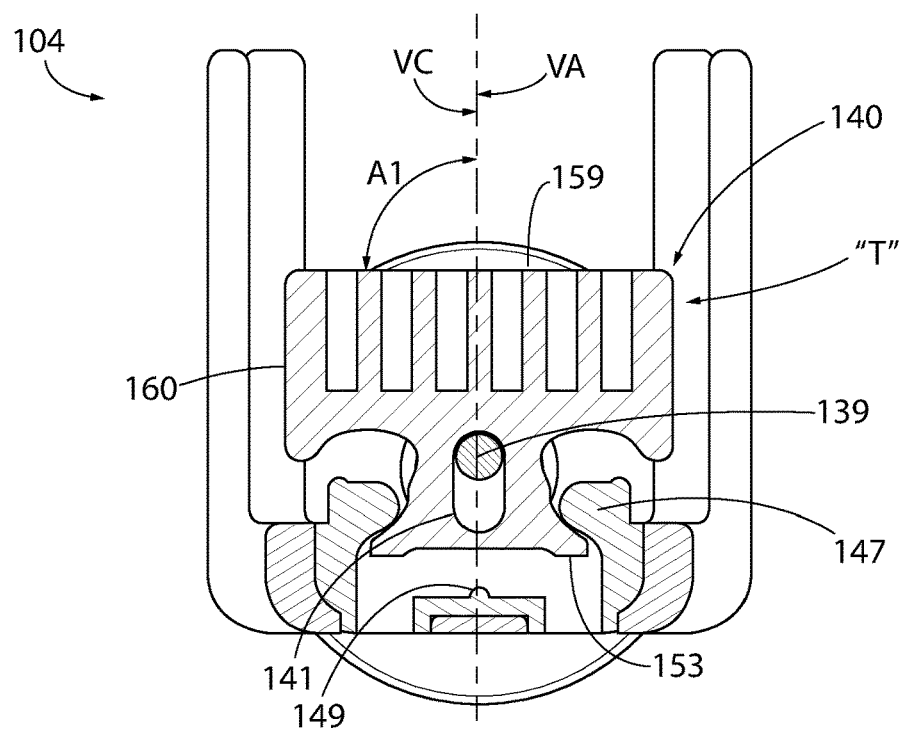

Tuft block 140 is movable in an oscillation cycle through a lowermost bottom vertical position "B" shown in FIG. 4A and an uppermost top vertical position "T" shown in FIG. 4E via a combination of vertical raising/lowering, lateral, and tilting motions, as further described herein.

The oscillation cycle will be described for convenience without limitation with arbitrarily locating tuft block 140 in a starting position at the bottom vertical position "B" shown in FIG. 4A. Tuft block 140 is in an upright orientation wherein top surface 159 of the tuft block faces upwards and is oriented at an angle A1 of approximately 90 degrees (i.e. perpendicular) to vertical axis VA of head portion 104. Accordingly, tuft block 140 is not substantially tilted or angled to one side or the other of vertical axis VA such that the lateral sides 160 of the upper bristle holding portion 142 are each spaced approximately equidistant from and parallel to the vertical axis.

In the starting bottom vertical position "B", the bottom surface 156 of upper bristle holding portion 142 is in contact with or located proximate to top surface 157 of opposing flanges 147 (see FIG. 4A). Bottom surface 150 of tuft block base portion 143 is vertically spaced distally to flanges 147 and proximately to protuberance 149. In some embodiments, the bottom surface 150 may contact and rest on protuberance 149. In this upright orientation of tuft block 140, small lateral gaps may be present in some arrangements between reduced width intermediate portion 144 of the tuft block and the free ends of flanges 147 on the toothbrush head portion 104.

To further describe orientations of tuft block 140 with respect to vertical axis VA during an oscillation cycle, tuft block 140 may be considered to define a vertical centerline VC extending vertically through the tuft block and oriented perpendicular to top surface 159 of the upper bristle holding portion 142 (see, e.g. FIG. 4B). Vertical centerline VC is further defined as extending through drive shaft 130 and spaced equidistant between the lateral sides 160 of upper bristle holding portion 142. In the bottom vertical position "B" of tuft block 140 shown in FIG. 4A, vertical centerline VC is axially aligned and coincides with vertical axis VA of toothbrush head portion 104. It will be noted that vertical axis VA associated with toothbrush head portion 104 provides a fixed or stationary point of reference on toothbrush head portion 104 while vertical centerline VC provides an angularly movable point of reference depending on the various tilted or canted orientation of tuft block 140 reached during different times or points in an oscillation cycle, as further described herein.

Referring to FIG. 4B, the next step in the method includes partially rotating the drive shaft using motor 170 (clockwise) through an angle of rotation less than 360 degrees which would represent one complete revolution of the drive shaft 130 and concomitantly one complete oscillation cycle of tuft block 140. During this initial partial shaft rotation, eccentric cam 139 begins to move clockwise about drive shaft 130. Through engagement of cam 139 with slot 141, the camming motion simultaneously begins to pivot or tilt tuft block 140 away from the vertical axis VA in a first lateral direction (i.e. left) such that vertical centerline VC is no longer axially aligned with vertical axis VA. The left lateral side 161 of intermediate portion 144 may translate laterally in position and come into contact with the left flange 147 which restricts the lateral displacement of tuft block 140 by cam 139.

Continuing rotation of the drive shaft 130 causes the tuft block 140 to further pivot and tilt laterally into a first fully tilted orientation "P1" shown in FIG. 4C facing outwards in a first lateral direction (i.e. to the left). Simultaneously, the tuft block 140 may move vertically upward slightly. A first tilt angle A2 is formed measured between vertical centerline VC and vertical axis VA. Angle A2 is less than 90 degrees and in some embodiments may be about 45 degrees or less. The degree to which tuft block 140 is tilted and angle A2 may be limited by contact between left side bottom surface 156 of upper bristle holding portion 142 and top surface 157 (e.g. rail 157a), and in some embodiments further or instead of by contact between one of the outwardly flared leg extensions 153 of base portion 143 (e.g. right side) with flange 147 or its respective concavely rounded shoulder 154 formed between the flange and wall 146b on the right side of tuft block 140 opposite the left flange engaging the bottom surface of the bristle holding portion and direction of tilt.

Further partial clockwise rotation of drive shaft 130 and eccentric cam 139 vertically raises the tuft block 140 towards the top vertical position "T" while at least partially or fully maintaining the first fully tilted orientation P1 during the translated vertical motion, as shown in FIG. 4D. During this rising motion, the right side outwardly flared leg extension 153 of base portion 143 maintains contact with and pivots about the right side flange 147 and/or the right shoulder 154 of toothbrush head portion 104. On the opposing side of tuft block 140, the left flange 147 slides downwards along curved lateral surface 155 on intermediate portion 144 (compare. FIGS. 4C and 4D).

Further partial clockwise rotation of the drive shaft 130 raises and pivots tuft block 140 back toward the vertical axis VA and into an upright orientation of the top vertical position "T" as shown in FIG. 4E. Top surface 159 of upper bristle holding portion 142 is returned to a position substantially perpendicular or 90 degrees (angle A1) to vertical VA such that the vertical centerline VC of tuft block 140 is axially aligned again and coincides with the vertical axis. Both outwardly flared leg extensions 153 of base portion 143 (right and left side) fully engage and contact their corresponding right and left flanges 147 and/or the shoulders 154 of toothbrush head portion 104 which limits the maximum vertical height reachable by the tuft block 140.

Figure 4F:
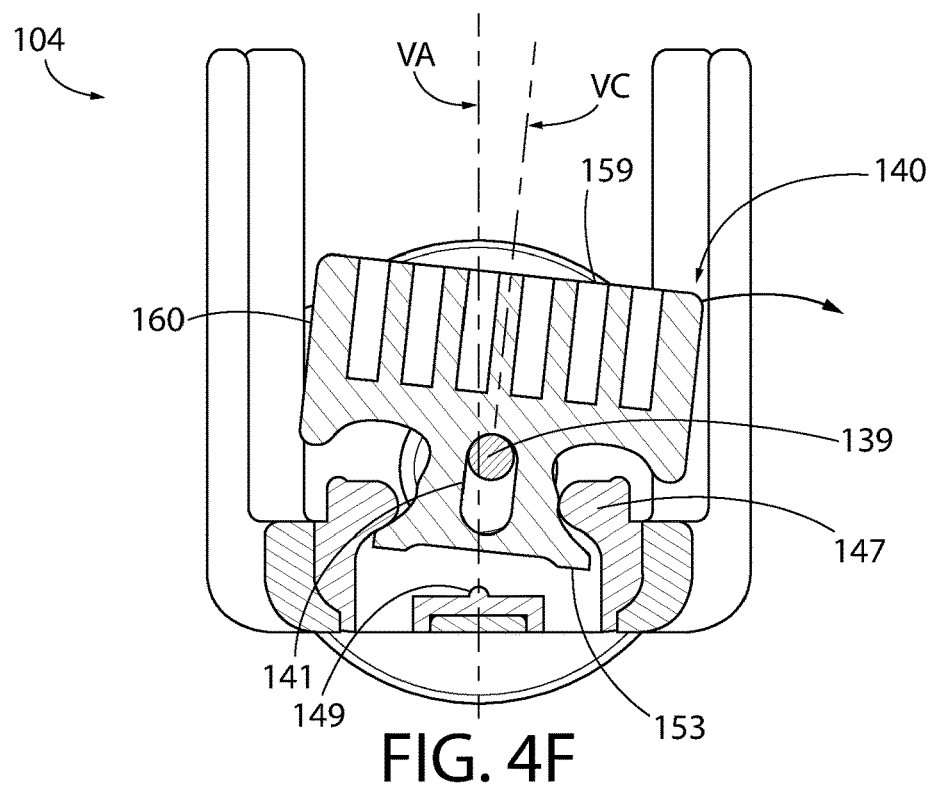

Referring to FIG. 4F, the method continues by partially rotating the drive shaft 130 producing a camming action in which cam 139 begins to pivot or tilt tuft block 140 away from the vertical axis VA in a second lateral direction (i.e.

right) such that vertical centerline VC is no longer axially aligned once again with vertical axis VA. The right lateral side 161 of intermediate portion 144 may translate laterally in position and come into contact with the right flange 147 which restricts the lateral displacement of tuft block 140 by cam 139.

Figure 4G:
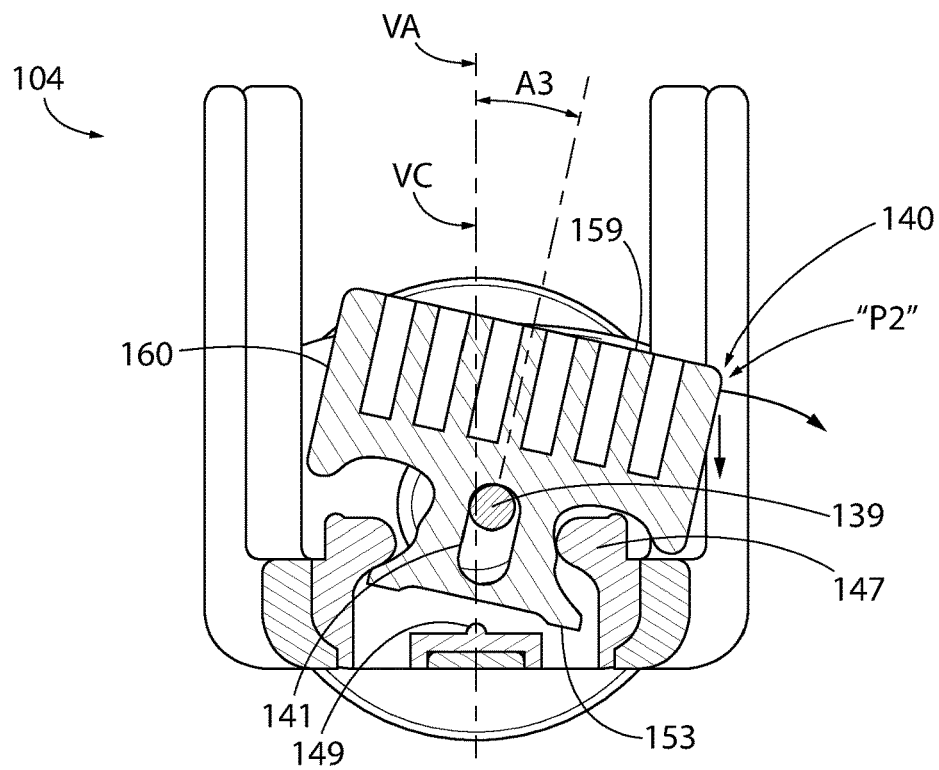

Continuing rotation of the drive shaft 130 causes the tuft block 140 to further pivot and tilt laterally into a second fully tilted orientation "P2" shown in FIG. 4G facing outwards in a second lateral direction (i.e. to the right). Simultaneously, the tuft block 140 may move vertically downward slightly. A second tilt angle A3 is formed measured between vertical centerline VC and vertical axis VA. Angle A3 is less than 90 degrees and in some embodiments may be about 45 degrees or less. In one embodiment, angle A3 may substantially equal to angle A2 of the first fully tilted position "P1" shown in FIG. 4C and described above. The degree to which tuft block 140 is tilted and angle A3 may be limited by contact between right side bottom surface 156 of upper bristle holding portion 142 and top surface 157 (e.g. rail 157*b*), and in some embodiments further or instead of by contact between one of the outwardly flared leg extensions 153 of base portion 143 (e.g. left side) with flange 147 or its respective concavely rounded shoulder 154 formed between the flange and wall 146*a* on the left side of tuft block 140 opposite the right flange engaging the bottom surface of the bristle holding portion and direction of tilt.

Further partial clockwise rotation of drive shaft 130 and eccentric cam 139 vertically lowers the tuft block 140 towards the bottom vertical position "B" while at least partially or fully maintaining the second fully tilted orientation P2 during the translated vertical motion, as shown in FIG. 4G. During this lowering motion, the left side outwardly flared leg extension 153 of base portion 143 maintains contact with and pivots about the left side flange 147 and/or the left shoulder 154 of toothbrush head portion 104. On the opposing side of tuft block 140, the right flange 147 slides downwards along curved lateral surface 155 on intermediate portion 144 (compare. FIGS. 4F and 4G).

Figure 4H:
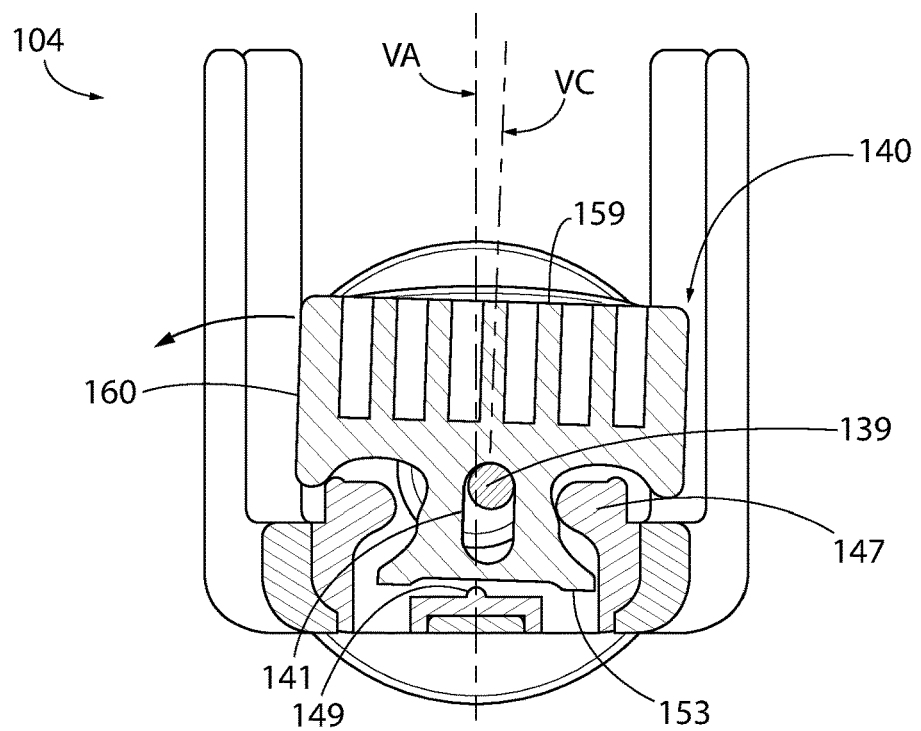

Further partial clockwise rotation of the drive shaft 130 as shown in FIG. 4H pivots and tilts the tuft block 140 back toward the vertical axis VA in the first lateral direction (i.e. left) and back towards bottom vertical position "B". During the action, contact may be broken between the left side outwardly flared leg extension 153 of base portion 143 the left side flange 147 and/or the left shoulder 154 of toothbrush head portion 104.

Figure 4I:
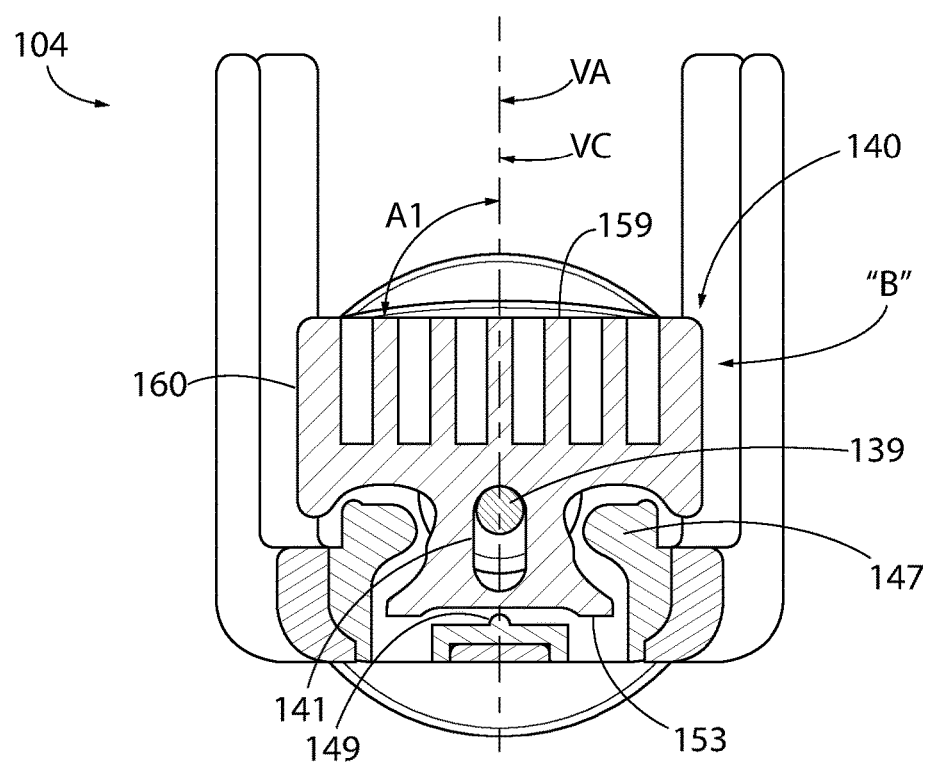

Referring to FIG. 4I, continuing partial clockwise rotation of drive shaft 130 returns tuft block 140 to the starting bottom vertical position "B" and an upright orientation as shown. This completes one oscillation cycle of tuft block 140 and a complete 360 degree revolution of drive shaft 130. The operation of toothbrush 100 and oscillating motions of tuft block 140 may continue by repeating the foregoing process steps.

Figure 5:
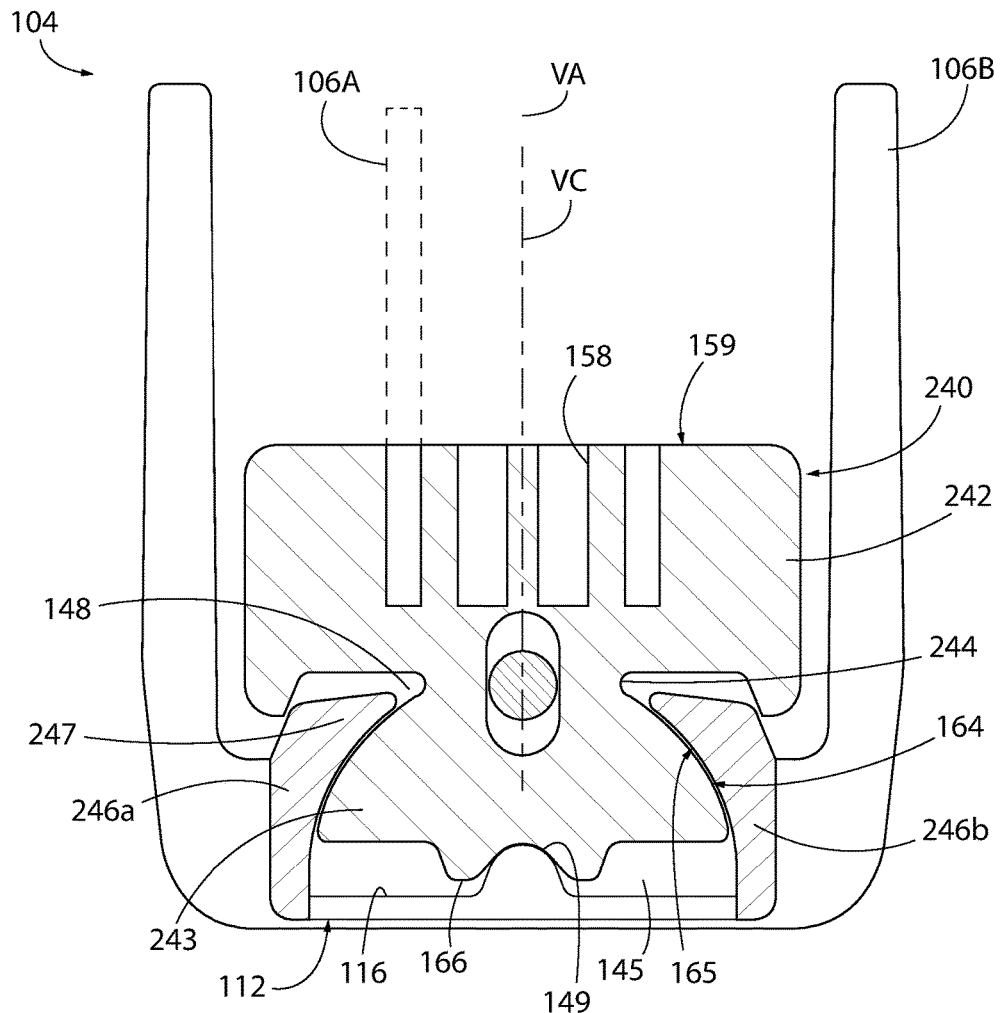
FIG. 5 is a transverse cross sectional view of an alternative embodiment of a movable tuft block.

FIG. 5 shows an alternative embodiment of toothbrush 100 in which tuft block 140 and head portion 104 are slightly reconfigured to provide lateral pivoting and tilting brushing motion only without vertical movement or displacement with respect to toothbrush head portion 104. In this configuration, tuft block 240 includes a base portion 243 having opposing convex arcuately curved bearing surfaces 164 configured for engaging complementary configured bearing surfaces 165 formed in receptacle 145 of toothbrush head portion 104. The concave arcuately curved bearing surfaces 165 may be formed on opposing receptacle walls 246*a*, 246*b* which further define opposing flanges 247 extending inwardly towards vertical axis VA. Flanges 247 are formed on a top portion of walls 246*a*, 246*b* and form a reduced width entrance 148 to receptacle 145 from front side 111 of toothbrush head 110 that precludes withdrawal of tuft block 240 through the front side.

The intermediate portion 244 of tuft block 240 may be severely truncated in height in contrast to intermediate portion 144 of tuft block 140 (see, e.g. FIG. 3) since this embodiment does not translate axially in a vertical direction. Base portion 243 defines a bottom surface 250 which engages pivot protuberance 149 in a similar manner to that already described for tuft block 140. In this embodiment, a pair of laterally spaced and downwardly extending ribs 166 may be provided between which protuberance 149 is received. Ribs 166 may be axially elongated in length along the longitudinal axis LA in toothbrush head portion 104 similarly to protuberance 149.

In operation, rotating drive shaft 130 oscillates tuft block 240 laterally sideways in opposing rocking or tilting motions and directions about central axis CA of the drive shaft via engagement of cam 139 with slot 141 in the tuft block. The vertical centerline VC of tuft block 240 will alternatingly be disposed at various angles to vertical axis VA of toothbrush head portion 104 during the oscillating motions. It should be noted that components not numbered in FIG. 5 are similar to the same components labeled in FIG. 3 unless specifically noted otherwise.

Figure 6A:
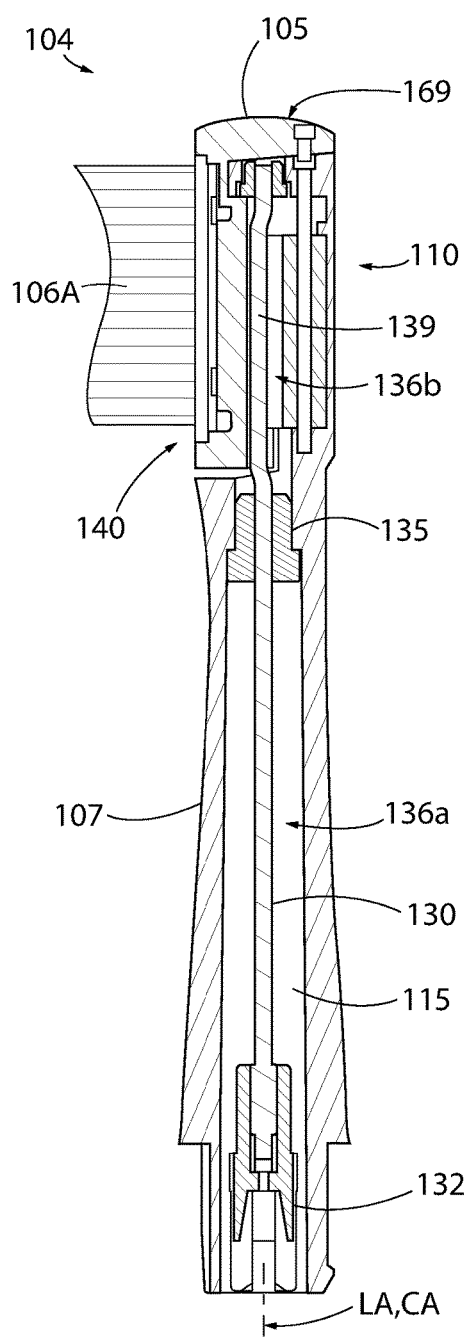
FIGS. 6A and 6B are side cross sectional and top plan views respectively of an alternative embodiment of a powered toothbrush head portion.
Figure 6B:
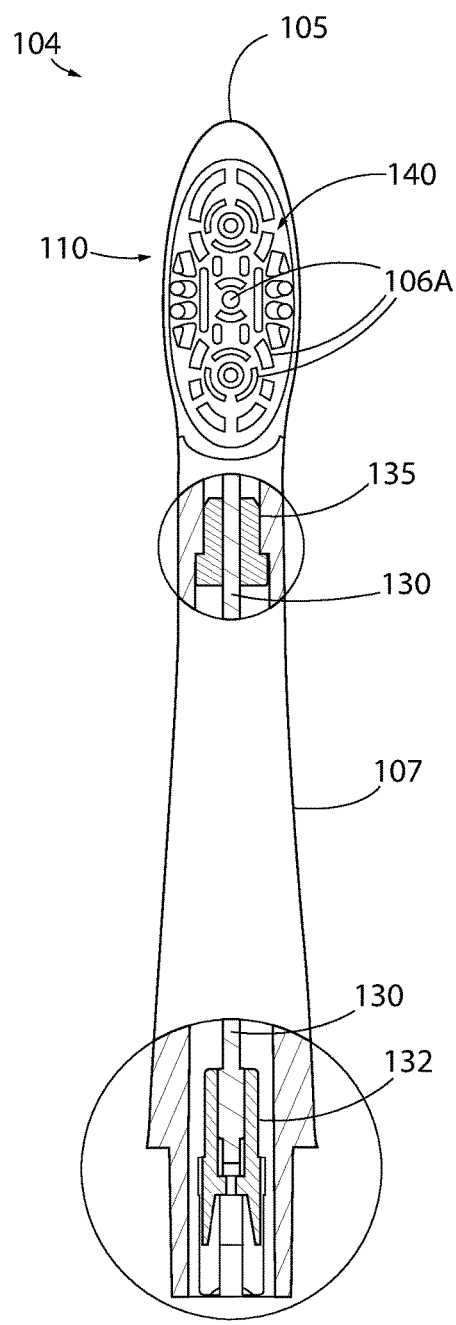

FIGS. 6A and 6B depict an alternative embodiment of toothbrush head portion 104 which includes a single oscillating tuft block 140. In this embodiment, tuft block has a generally oval shape (in top plan view) and is disposed near distal end 105 of toothbrush head 110. The tooth motor driven cleaning elements 106A comprise a plurality of bristles and elastomeric elements as shown. The tuft block 140 may be configured as shown in FIG. 3 for replicating Bass type brushing motions, or alternatively may be configured as shown in FIG. 5 for producing only lateral back and forth pivoting or tilting brushing action with respect to longitudinal axis LA.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:
1. A powered toothbrush head comprising:
a head portion comprising a longitudinal axis and a cavity in a front side of the head portion;
a rotatable drive shaft extending through the head portion into the cavity, the drive shaft defining a first axis of rotation and including a first cam;
a first movable tuft block disposed at least partially in the cavity and having an elongated slot operably engaged with the cam;

the first movable tuft block including an upper portion configured for retaining tooth cleaning elements, a lower base portion, and a reduced width intermediate portion between the upper and base portions; and wherein the first movable tuft block is movable in a combination oscillating motion about the longitudinal axis comprising vertical motion and tilting motion upon rotation of the drive shaft.

2. The powered toothbrush head of claim 1, wherein the intermediate portion has a lateral width measured transversely to the longitudinal axis that is less than lateral widths of the adjoining upper and base portions of the first movable tuft block.

3. The powered toothbrush head of claim 1, wherein the cavity includes an opposing pair of laterally spaced apart flanges extending inwardly towards the longitudinal axis, the flanges being arranged to receive the intermediate portion of the first movable tuft block between the flanges.

4. The powered toothbrush head of claim 3, wherein the base portion of the first movable tuft block has a lateral width that is larger than a width measured between the flanges so that the tuft block cannot be withdrawn from the cavity in a direction transverse to the longitudinal axis.

5. The powered toothbrush head of claim 3, wherein the upper portion of the first movable tuft block has a lateral width that is larger than a width measured between the flanges.

6. The powered toothbrush head of claim 1, wherein the upper, intermediate, and base portions of the first movable tuft block collectively defines a lateral periphery extending circumferentially around the first movable tuft block that is not attached to the head portion; and wherein the first movable tuft block is free floating within the cavity.

7. The powered toothbrush head of claim 1, wherein the base portion of the first movable tuft block has a bottom surface that engages a protuberance defining a pivot formed on a bottom of the cavity in the head portion, wherein the pivot is an axially elongated longitudinally-extending ridge.

8. The powered toothbrush head of claim 1, wherein the cam has a cylindrical shape and is formed by an offset segment of the drive shaft.

9. The powered toothbrush head of claim 1, further comprising a second movable tuft block configured for retaining tooth cleaning elements, the second movable tuft block having a second axis of rotation that is perpendicular to the first axis of rotation, wherein the second movable tuft block is movable in back and forth oscillating arcuate motions about the second axis of rotation.

10. A powered toothbrush comprising:
a handle portion comprising a motor;
a head portion comprising a longitudinal axis, the head portion including a rear wall and lateral side walls defining an open cavity;
a rotatable cylindrical drive shaft operably connected to the motor and extending through the head portion into the cavity, the drive shaft defining a first axis of rotation and having an axially offset segment defining a first cam;
a first movable tuft block disposed at least partially in the cavity and having a vertically elongated slot operably engaged with the first cam;
the first movable tuft block including an upper portion configured for retaining tooth cleaning elements, a lower base portion, and a reduced width intermediate portion connected between the upper and base portions; and
wherein the first movable tuft block is movable in a combination oscillating motion about the longitudinal axis comprising a vertical motion and a tilting motion produced by rotation of the drive shaft.

11. The powered toothbrush of claim 10, wherein the head portion includes an opposing pair of laterally spaced apart flanges extending inwardly towards the longitudinal axis to define an entrance to a receptacle disposed in a lower portion of the cavity, the flanges being arranged to receive the intermediate portion of the first movable tuft block between the flanges.

12. The powered toothbrush of claim 11, wherein the entrance to the receptacle has a lateral width that is less than the width of the base portion of the first movable tuft block which is movably trapped in the receptacle.

13. The powered toothbrush of claim 11, wherein the base portion of the first movable tuft block includes a concavely curved surface disposed on either lateral side of the base portion, each curved surface being arranged and operable to alternatingly engage a respective flange during a tilting motion of the first movable tuft block, wherein the curved surfaces simultaneously engage the flanges during a vertical motion of the first movable tuft block.

14. The powered toothbrush of claim 10, wherein the drive shaft includes proximal and distal ends, the proximal end being configured for detachably engaging the motor and the distal end being a curved end defining a second cam for oscillating a second movable tuft block disposed in the head portion, and further comprising the second movable tuft block having a second axis of rotation that is perpendicular to the first axis of rotation, wherein the second movable tuft block is movable in back and forth oscillating arcuate motions about the second axis of rotation.

* * * * *